United States Patent
Tomita

(10) Patent No.: US 8,322,374 B2
(45) Date of Patent: Dec. 4, 2012

(54) CHANNEL SWITCHING VALVE

(75) Inventor: Masami Tomita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 254 days.

(21) Appl. No.: 12/747,996

(22) PCT Filed: Dec. 17, 2008

(86) PCT No.: PCT/JP2008/073012
§ 371 (c)(1),
(2), (4) Date: Jul. 14, 2010

(87) PCT Pub. No.: WO2009/078450
PCT Pub. Date: Jun. 25, 2009

(65) Prior Publication Data
US 2010/0269936 A1   Oct. 28, 2010

(30) Foreign Application Priority Data
Dec. 17, 2007   (JP) ................ 2007-324793

(51) Int. Cl.
*F16K 11/074* (2006.01)
*F16K 11/06* (2006.01)

(52) U.S. Cl. ............ 137/625.46; 137/625.11; 251/337

(58) Field of Classification Search ............ 137/625.46, 137/625.11; 251/337
See application file for complete search history.

(56) References Cited

U.S. PATENT DOCUMENTS

| | | | | |
|---|---|---|---|---|
| 1,457,957 A * | 6/1923 | Birkigt | .......................... | 251/337 |
| 2,089,943 A * | 8/1937 | Busby | ...................... | 137/625.46 |
| 2,317,407 A * | 4/1943 | Samiran | .................... | 137/625.11 |
| 2,377,473 A * | 6/1945 | Wolcott | .................... | 137/625.11 |
| 2,438,447 A * | 3/1948 | Maynard | .................. | 137/625.46 |
| 2,449,733 A * | 9/1948 | Wilkening | ................ | 137/625.11 |
| 2,516,795 A * | 7/1950 | Norton | .......................... | 251/337 |
| 5,295,520 A * | 3/1994 | Acker | ....................... | 137/625.46 |
| 6,311,661 B1 * | 11/2001 | Kobayashi et al. | ........... | 251/337 |
| 6,729,350 B2 * | 5/2004 | Schick | ....................... | 137/625.46 |
| 2004/0099319 A1 * | 5/2004 | Monti | ....................... | 137/625.46 |

FOREIGN PATENT DOCUMENTS

JP    62-56858 A    3/1987

(Continued)

OTHER PUBLICATIONS

International Search Report for the Application No. PCT/JP2008/073012 mailed Jan. 20, 2009.

(Continued)

*Primary Examiner* — John Rivell
(74) *Attorney, Agent, or Firm* — Cheng Law Group, PLLC

(57) ABSTRACT

A channel switching valve is disclosed. The channel switching valve has a stator and a body section each having a connecting surface. The stator and the body section are removably fixed to each other by bolts at their connecting surfaces. Each of the connecting surfaces has a protruding/recessed pattern formed thereon, and the patterns are designed to fit into each other. By rotating the stator and the body section relative to each other, the stroke of a spring is changed between a position where the protruding/recessed patterns of the stator and the body section are fitted into each other and a position where they are not fitted into each other. The spring is held in the body section in its compressed state to urge the rotor toward the stator. An urging force for pressing the rotor against the stator is adjusted by changing the stroke of the spring.

2 Claims, 5 Drawing Sheets

FOREIGN PATENT DOCUMENTS

| | | |
|---|---|---|
| JP | 1-307575 A | 12/1989 |
| JP | 3-15708 U | 2/1991 |
| JP | 4-62970 U | 5/1992 |
| JP | 2005-76858 A | 3/2005 |
| JP | 2006-292392 A | 10/2006 |

OTHER PUBLICATIONS

Notification of Reasons for Refusal for the Application No. 2009-546292 from Japan Patent Office mailed Nov. 29, 2011.

\* cited by examiner

CHANNEL SWITCHING VALVE

BACKGROUND OF THE INVENTION

1. Field of the Invention

The present invention relates to a channel switching valve for use in liquid chromatographs and the like.

2. Description of the Related Art

High-performance liquid chromatographs have a flow channel, through which liquid flows under high pressure, and require channel switching.

For such a purpose, a channel switching valve is conventionally used. A conventional channel switching valve includes a stator to be connected to flow channels and a rotor, and is configured to perform channel switching by rotating the rotor in a state where the stator and the rotor are in contact with each other at their surfaces (see Japanese Unexamined Patent Publication No. 1-307575).

In such a channel switching valve, the contact surface of the stator has ports to be connected to flow channels and the contact surface of the rotor has a switching groove for interconnecting two of the ports of the contact surface of the stator. The stator is interposed between a housing top, to which flow channels are to be connected, and the rotor. The stator may be separately formed from the housing top or formed integrally therewith. The rotor is attached to the distal end of a rotary shaft, and is pressed against the stator by an elastic member, such as a spring, with a force required to allow the switching groove to be liquid-tight. That is, the rotor and the stator are in contact with each other at their surfaces, thereby preventing liquid leakage from the switching groove. The rotor is rotated by receiving a rotational driving force from the rotary shaft. In order to perform channel switching, the connection between the ports of the stator is changed by rotating the rotor.

In the case of such a conventional channel switching valve, the rotor is made of a soft material, such as resin, and the stator is made of a material harder than that of the rotor, such as stainless steel. Therefore, the contact surface of the rotor is worn out due to the prolonged use of the channel switching valve. This may cause an increase in the rotational torque of the channel switching valve, fluid leakage, and cross-contamination by liquid remaining in the worn-out contact surface of the rotor.

Further, as described above, the rotor is pressed against the stator by a given force to prevent liquid leakage. Therefore, in a case where the rotor is made of resin, the contact surface of the rotor is scraped off and scrapings are generated by friction caused by the rotation of the rotor. In this case, the scrapings from the rotor also flow into a column connected downstream from the channel switching valve, which becomes the cause of deterioration of the column.

On the other hand, the rotor may be made of a hard material such as ceramics. In this case, unlike the rotor made of resin, scrapings are not generated, but it is necessary to reduce surface roughness of contact surfaces of both the stator and the rotor and to achieve high flatness of these contact surfaces to maintain sealing. However, if such contact surfaces are pressed against each other by a great force, a so-called "linking" phenomenon in which mirror-polished surfaces adhere to each other occurs, which interferes with the rotation of the rotor.

In order to maintain liquid-tightness achieved by the rotor and the stator, the rotor is often made of resin. In this case, however, there is a problem that the rotor always pressed against the stator by a great force is significantly worn out by its rotation, which leads to a shorter life expectancy of the valve.

In a case where a channel switching valve needs to be liquid-tight under conditions where liquid flows under high pressure, a rotor needs to be pressed against a stator by a great force. However, in some cases, for example, when liquid is allowed to flow under low pressure, such a great pressing force is not required depending on the intended purpose. Despite this, in the case of conventional channel switching valves, the pressing force of a rotor against a stator is constant and cannot be changed.

SUMMARY OF THE INVENTION

It is therefore an object of the present invention to provide a channel switching valve having improved durability.

The channel switching valve according to the present invention includes a body section, a pair of a stator having a contact surface and a rotor having a contact surface, the contact surfaces being in contact with each other, an elastic member which urges the rotor toward the stator, and an adjusting system which adjusts an urging force for pressing the rotor against the stator by changing the stroke of the elastic member.

The stator, to which a plurality of flow channels are to be connected, has a surface having distribution ports to be connected to the flow channels respectively, and is attached to the body section so that the surface faces inward. The rotor is placed in the body section, has a contact surface being in contact with the surface of the stator and having at least one groove for interconnecting two of the distribution ports of the stator, and is attached to a distal end of a shaft penetrating the body section. The rotor is rotated by rotating the shaft so that a combination of the distribution ports that should be interconnected by the groove is changed. The elastic member is held in the body section in its compressed state.

According to one embodiment of the present invention, the stator and the body section each have a connecting surface, and are removably fixed to each other by a fixing member at their connecting surfaces. In this case, the adjusting system includes, for example, a protruding/recessed pattern formed on the connecting surface of the stator and a protruding/recessed pattern formed on the connecting surface of the body section. The protruding/recessed patterns of the stator and the body section are designed to be fitted into each other. By rotating the stator and the body section relative to each other, the stroke is changed between a position where the stator and the body section are fixed to each other in a state where their protruding/recessed patterns are fitted into each other and a position where the stator and the body section are fixed to each other in a state where their protruding/recessed patterns are not fitted into each other.

According to another embodiment of the present invention, the shaft to which the rotor is attached and the rotor each have a connecting surface, and are removably fixed to each other by a fixing member at their connecting surfaces. In this case, the adjusting system includes, for example, a protruding/recessed pattern formed on the connecting surface of the shaft and a protruding/recessed pattern formed on the connecting surface of the rotor. The protruding/recessed patterns of the shaft and the rotor are designed to be fitted into each other. By rotating the shaft and the rotor relative to each other, the stroke is changed between a position where the shaft and the rotor are fixed to each other in a state where their protruding/recessed patterns are fitted into each other and a position where the shaft and the rotor are fixed to each other in a state where their protruding/recessed patterns are not fitted into each other.

According to the present invention, the stroke of the elastic member urging the rotor toward the stator can be changed by the adjusting system. Therefore, a pressing force applied by the elastic member can be reduced when liquid is allowed to flow under low pressure, which makes it possible to increase the lifetime of the valve.

Further, the stroke of the elastic member can be more easily changed by providing, as the adjusting system, a protruding/recessed pattern on connecting surfaces of both the stator and the rotor or on connecting surfaces of both the rotor and the shaft. In this case, the stroke of the elastic member is changed depending on whether the protruding/recessed patterns of the connecting surfaces are fitted into each other or not.

Figure 1A:
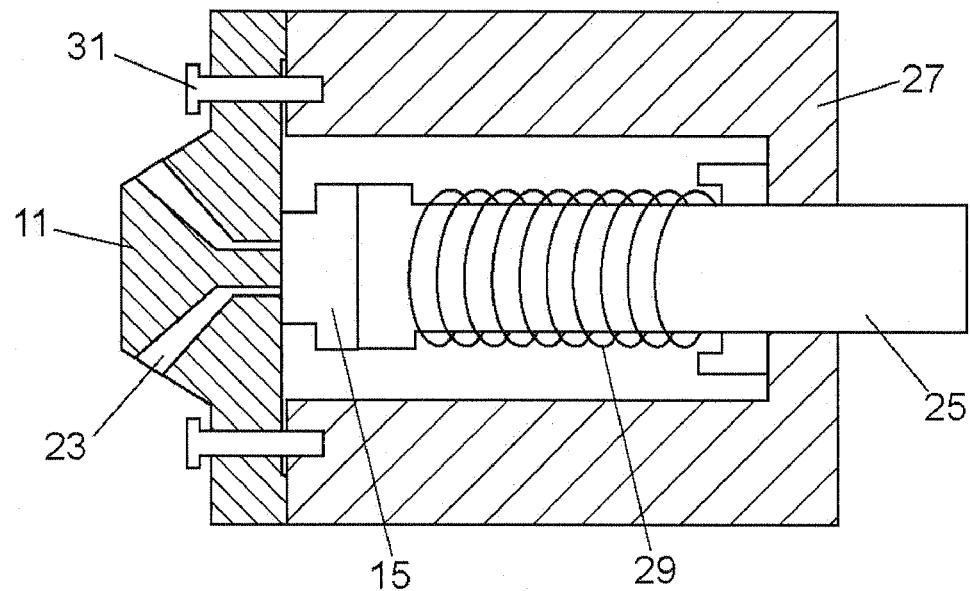
FIG. 1A is a schematic sectional view of a channel switching valve according to a first embodiment of the present invention in a state where the stroke of a spring is shortened.

DESCRIPTION OF THE REFERENCE NUMERALS 11 stator
12, 26 protruding/recessed portion
13 contact surface
15 rotor
17 contact surface
19 distribution port
21 groove
22 flange
23 channel connecting portion
25 shaft
27 body section
29 spring
31 bolt

DETAILED DESCRIPTION OF THE INVENTION

Hereinbelow, some embodiments of the present invention will be described with reference to the accompanying drawings.

First Embodiment

Figure 1B:
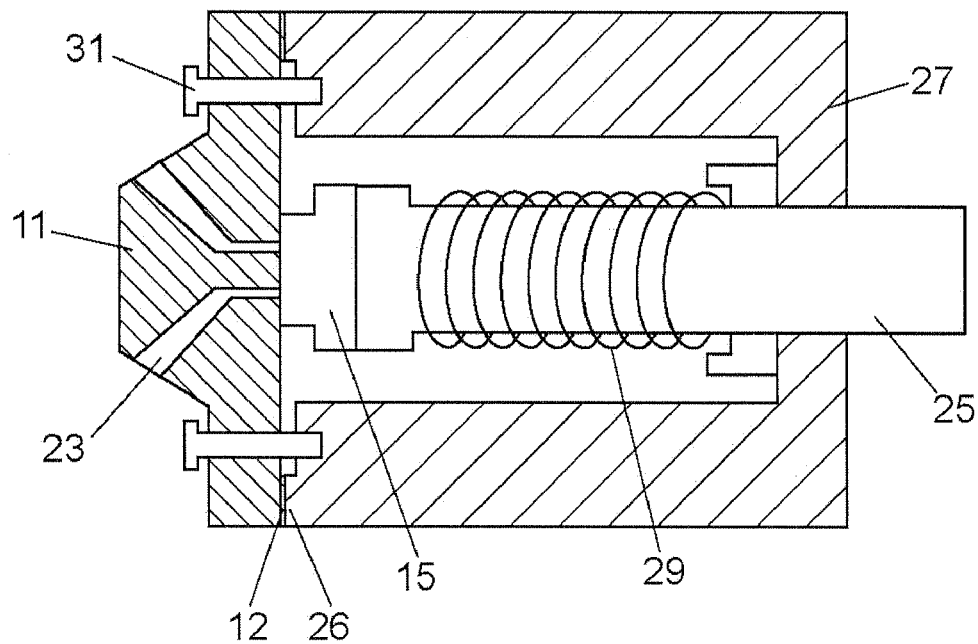
FIG. 1B is a schematic sectional view of the channel switching valve according to the first embodiment of the present invention in a state where the stroke of the spring is lengthened.
Figure 2A:
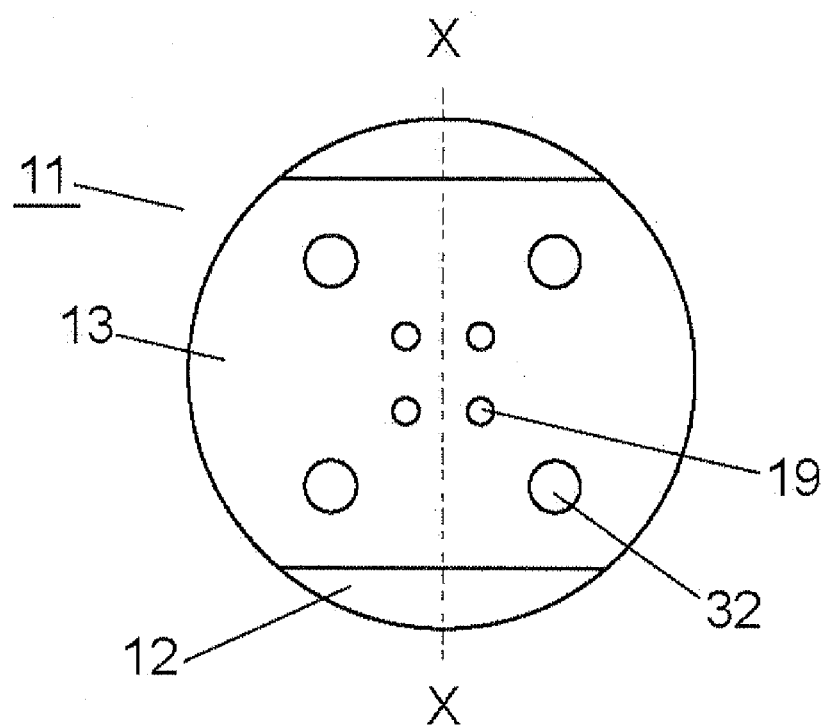
FIG. 2A is a plan view of a stator of the channel switching valve according to the first embodiment of the present invention when viewed from its contact surface side.
Figure 2B:
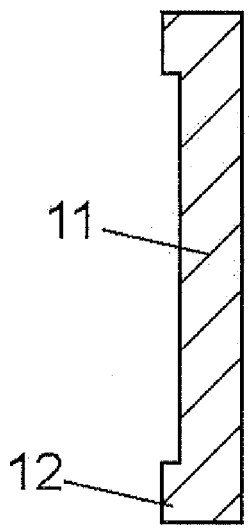
FIG. 2B is a sectional view taken along the X-X line in FIG. 2A.
Figure 3A:
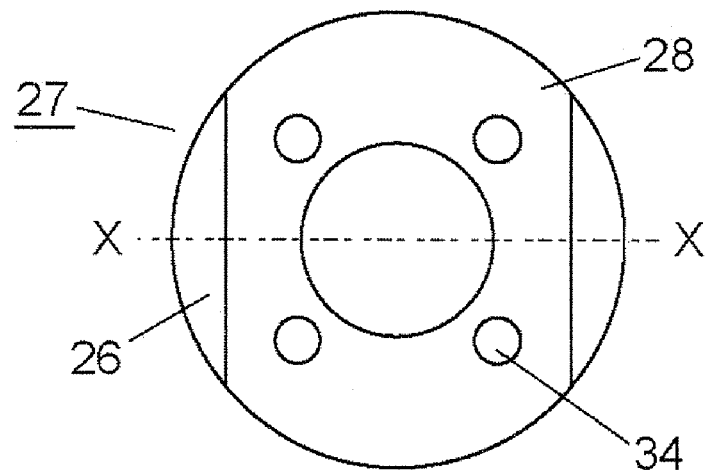
FIG. 3A is a plan view of a body section of the channel switching valve according to the first embodiment of the present invention when viewed from the stator side.
Figure 3B:
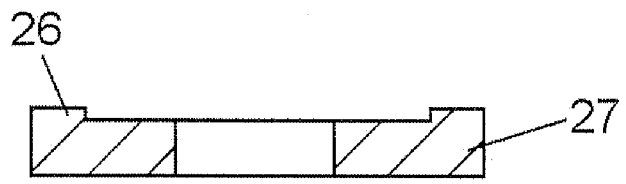
FIG. 3B is a sectional view taken along the X-X line in FIG. 3A.
Figure 3C:
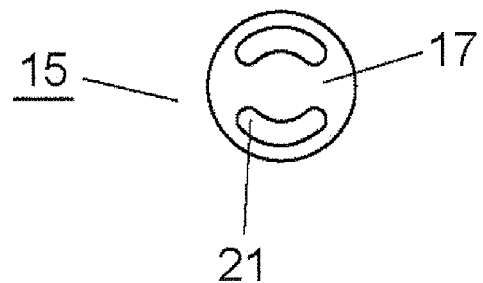
FIG. 3C is a plan view of a rotor placed in the body section of the channel switching valve according to the first embodiment of the present invention when viewed from its contact surface side.

FIGS. 1A and 1B are schematic views showing the structure of a channel switching valve according to a first embodiment of the present invention. FIG. 1A and FIG. 1B show two states of the channel switching valve, between which the stroke of a coil spring as an elastic member is changed by rotating one of a stator 11 and a body section 27. More specifically, FIG. 1A shows a state where the stroke is shortened and FIG. 1B shows a state where the stroke is lengthened. FIGS. 2A and 2B show the stator 11 of the channel switching valve according to the first embodiment of the present invention, FIGS. 3A and 3B show the body section 27 of the channel switching valve according to the first embodiment of the present invention, and FIG. 3C shows a rotor 15 placed in the body section 27.

The stator 11 is made of stainless steel, and is integrally formed with a housing top to which flow channels are to be connected. The stator 11 has a contact surface 13 being in contact with the rotor 15, and is attached to the body section 27 so that the contact surface 13 faces inward. The body section 27 is fixed to the periphery of the stator 11 by bolts 31. The stator 11 has a plurality of channel connecting portions 23, and the contact surface 13 of the stator 11 has, in its region being in contact with a contact surface 17 of the rotor 15, distribution ports 19 connected to the channel connecting portions 23 respectively.

The rotor 15 is placed in the body section 27 and is attached to the distal end of a shaft 25 penetrating the body section 27. The contact surface 17 of the rotor 15 is in contact with the contact surface 13 of the stator 11 and has arc-shaped grooves 21 each of which interconnects two of the distribution ports 19 of the stator 11.

The shaft 25 is rotatably supported by the body section 27. In the body section 27, an elastic member such as a coil spring 29 is provided around the shaft 25. The spring 29 is inserted between the rotor 15 and the body section 27 in its compressed state, and therefore, the rotor 15 is urged by the spring 29 toward the stator 11.

The number of the channel connecting portions 23, the number of the distribution ports 19, and the number of the grooves 21 are not particularly limited. In this embodiment, four channel connecting portions 23, four distribution ports 19, and two grooves 21 are provided.

In order to perform channel switching, the connection between the distribution ports 19 and the groove 21 is changed by rotating the shaft 25, that is, by slidably rotating the rotor 15 relative to the stator 11.

The rotor 15 is made of, for example, resin. The rotor 15, made of resin, needs to be replaced with a new one when worn out. In the first embodiment of the present invention, the stator 11 is made of metal and the rotor 15 is made of resin. This is because the rotor 15 is more easily fabricated than the stator 11. However, unlike the first embodiment of the present invention, the stator 11 may be made of resin and the rotor 15 may be made of a metal such as stainless steel.

Referring to FIGS. 2 and 3, the contact surface 13 of the stator 11 has a protruding/recessed pattern 12 formed thereon, and a contact surface 28 of the body section 27 has a protruding/recessed pattern 26 formed thereon. The protruding/recessed patterns 12 and 26 are designed to be fitted into each other. The protruding/recessed pattern 12 has two protrusions formed on the periphery of the contact surface 13 so as to be opposed to each other. The protruding/recessed pattern 26 also has two protrusions formed on the periphery of the contact surface 28 so as to be opposed to each other. The protruding/recessed patterns 12 and 26 are formed in such a manner that the protrusions of one of the protruding/recessed patterns are fitted into a recess of the other protruding/recessed pattern, and the recess of the one protruding/recessed pattern is fitted into the protrusions of the other protruding/recessed pattern when one of the protruding/recessed patterns 12 and 26 is rotated relative to the other by 90° from a position where the protrusions of the protruding/recessed pattern 12 and the protrusions of the protruding/recessed pattern 26 face each other.

A difference in surface level between the protrusion and the recess (i.e., the thickness of the protrusion) of each of the protruding/recessed patterns 12 and 26 is, for example, about 0.5 mm, but is not particularly limited and is set depending on the spring constant of the spring 29.

The contact surface 13 of the stator 11 has a plurality of bolt holes 32 so that the stator 11 and the body section 27 can be removably fixed to each other by screwing the bolts 31 into the bolt holes 32 and matching bolt holes 34 of the body section 27. The bolt holes 32 and the bolt holes 34 are provided so that the stator 11 and the body section 27 can be fixed to each other in two different positions, one being a position where the protrusions of the protruding/recessed pattern 12 and the protrusions of the protruding/recessed pattern 26 face each other and the other being a position achieved by rotating one of the protruding/recessed patterns 12 and 26 relative to the other by 90° from the above position so that the protrusions of one of the protruding/recessed patterns 12 and 26 are fitted into the recess of the other.

FIG. 1A shows a state where the stator 11 and the body section 27 are fixed to each other with the protrusions of one of the protruding/recessed patterns 12 and 26 being fitted into the recess of the other. In this state, no gap is created between the stator 11 and the body section 27, that is, the stroke of the spring 29 urging the rotor 15 toward the stator 11 is shortened, and therefore, the spring force of the spring 29 is increased, thereby increasing the pressing force of the rotor 15 against the stator 11. The channel switching valve is set to this state when used in a flow channel through which liquid flows under high pressure.

On the other hand, the channel switching valve can be brought into a state shown in FIG. 1B by removing the bolts 31 from the channel switching valve being in a state shown in FIG. 1A, rotating the stator 11 by 90° relative to the body section 27, and tightening the bolts 31 again. In this state, the protruding/recessed pattern 12 of the stator 11 and the protruding/recessed pattern 26 of the body section 27 are not fitted into each other, that is, the protrusions of the protruding/recessed pattern 12 and the protrusions of the protruding/recessed pattern 26 are in contact with each other so that the stator 11 and the body section 27 are separated from each other by a distance equal to the total of the height of the protrusion of the protruding/recessed pattern 12 and the height of the protrusion of the protruding/recessed pattern 26. As a result, the stroke of the spring 29 urging the rotor 15 toward the stator 11 is lengthened, and therefore, the spring force of the spring 29 is reduced, thereby reducing the pressing force of the rotor 15 against the stator 11. The channel switching valve is set to this state when used in a flow channel through which liquid flows under low pressure. In this state, the abrasion of the rotor 15 is reduced because of a reduction in the pressing force of the rotor 15 against the stator 11.

Second Embodiment

Figure 4A:
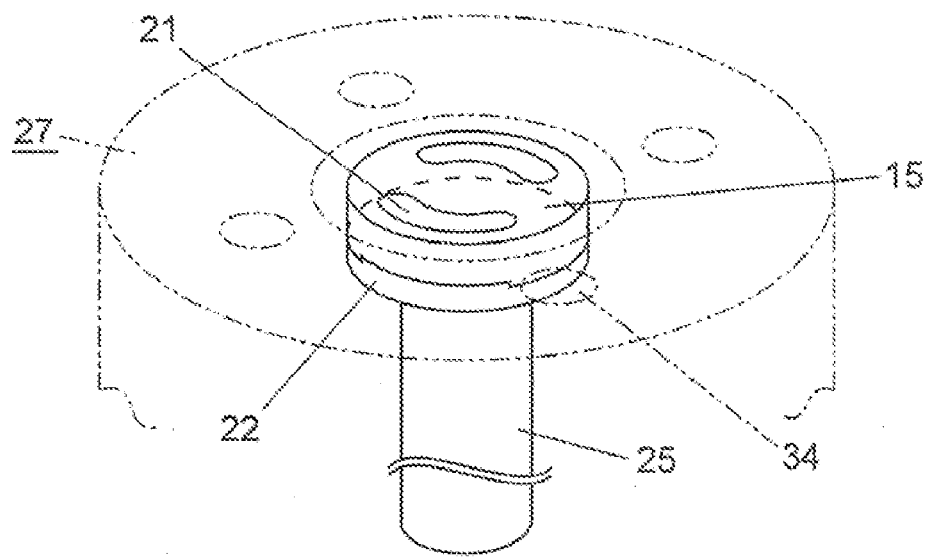
FIGS. 4A and 4B are perspective views of a rotor and a shaft of a channel switching valve according to a second embodiment of the present invention.
Figure 4B:
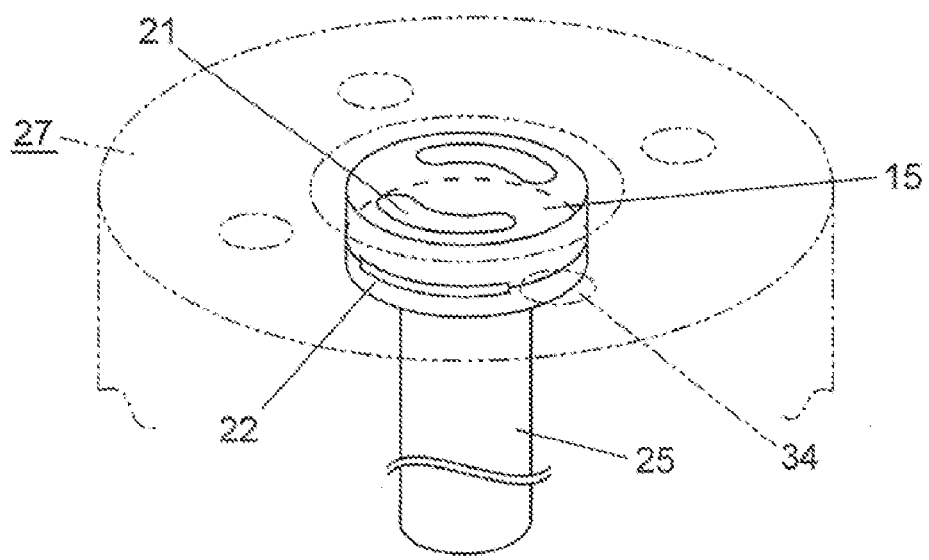

FIGS. 4A and 4B are perspective views of the rotor 15 placed in the body section 27 and the shaft 25 of a channel switching valve according to a second embodiment of the present invention. The upper surface of the rotor 15 shown in FIG. 4 is a contact surface being in contact with the stator 11. The rotor 15 has the grooves 21 each of which interconnects the channel connecting portions of the stator 11. In the second embodiment, the stator 11 and the body section 27 remain fixed to each other, but the rotor 15 and the shaft 25 each have a connecting surface and are removably fixed to each other at their connecting surfaces.

The shaft 25 is rotatably supported by the body section 27, and a flange 22 is provided at the distal end of the shaft 25. The positioning of the rotor 15, that is, the fixation of the rotor 15 to the shaft 25 is achieved by attaching the rotor 15 to the flange 22 with bolts. The connecting surface of the flange 22 and the connecting surface of the rotor 15 each have a protruding/recessed pattern similar to that described above with reference to the first embodiment. Further, as in the case of the first embodiment of the present invention, an elastic member such as a coil spring is provided around the shaft 25 in the body section 27. More specifically, the elastic member is inserted between the flange 22 and the body section 27 in its compressed state so that the rotor 15 is urged by the spring toward the stator 11. Also in the second embodiment of the present invention, the distance between the connecting surface of the rotor 15 and the connecting surface of the flange 22 can be changed, that is, the stroke of the spring urging the rotor 15 toward the stator 11 can be changed by once removing the bolts from the rotor 15 and the flange 22, rotating the rotor 15 by 90° relative to the flange 22, and then tightening the bolts again.

FIG. 4A shows a state where the protruding/recessed pattern of the connecting surface of the rotor 15 and the protruding/recessed pattern of the connecting surface of the flange 22 are fitted into each other. In this state, the rotor 15 and the flange 22 are the closest to each other, that is, the stroke of the spring urging the rotor 15 toward the stator 11 is lengthened, and therefore, the spring force of the spring is reduced, thereby reducing the pressing force of the rotor 15 against the stator 11.

On the other hand, the channel switching valve being in a state shown in FIG. 4A can be brought into another state by removing the bolts, rotating the rotor 15 by 90° relative to the flange 22, and tightening the bolts again in a state where protrusions of the protruding/recessed pattern of the connecting surface of the rotor 15 and protrusions of the protruding/recessed pattern of the connecting surface of the flange 22 face each other as shown in FIG. 4B. In this state, the rotor 15 and the flange 22 are separated from each other by the distance equal to the total of the height of the protrusion of the protruding/recessed pattern of the rotor 15 and the height of the protrusion of the protruding/recessed pattern of the flange 22. Therefore, the distance between the flange 22 and the body section 27 is shortened, that is, the stroke of the spring urging the rotor 15 toward the stator 11 is shortened, and therefore the spring force of the spring is increased, thereby increasing the pressing force of the rotor 15 against the stator 11.

As described above, the stroke of the spring can be made variable by allowing the rotor 15 and the shaft 25 to be removably fixed to each other at their connecting surfaces. The channel switching valve according to the second embodiment of the present invention can also be used as a low-pressure valve when it is not necessary to allow liquid to flow under high pressure. This makes it possible to increase the lifetime of the valve.

Figure 5:
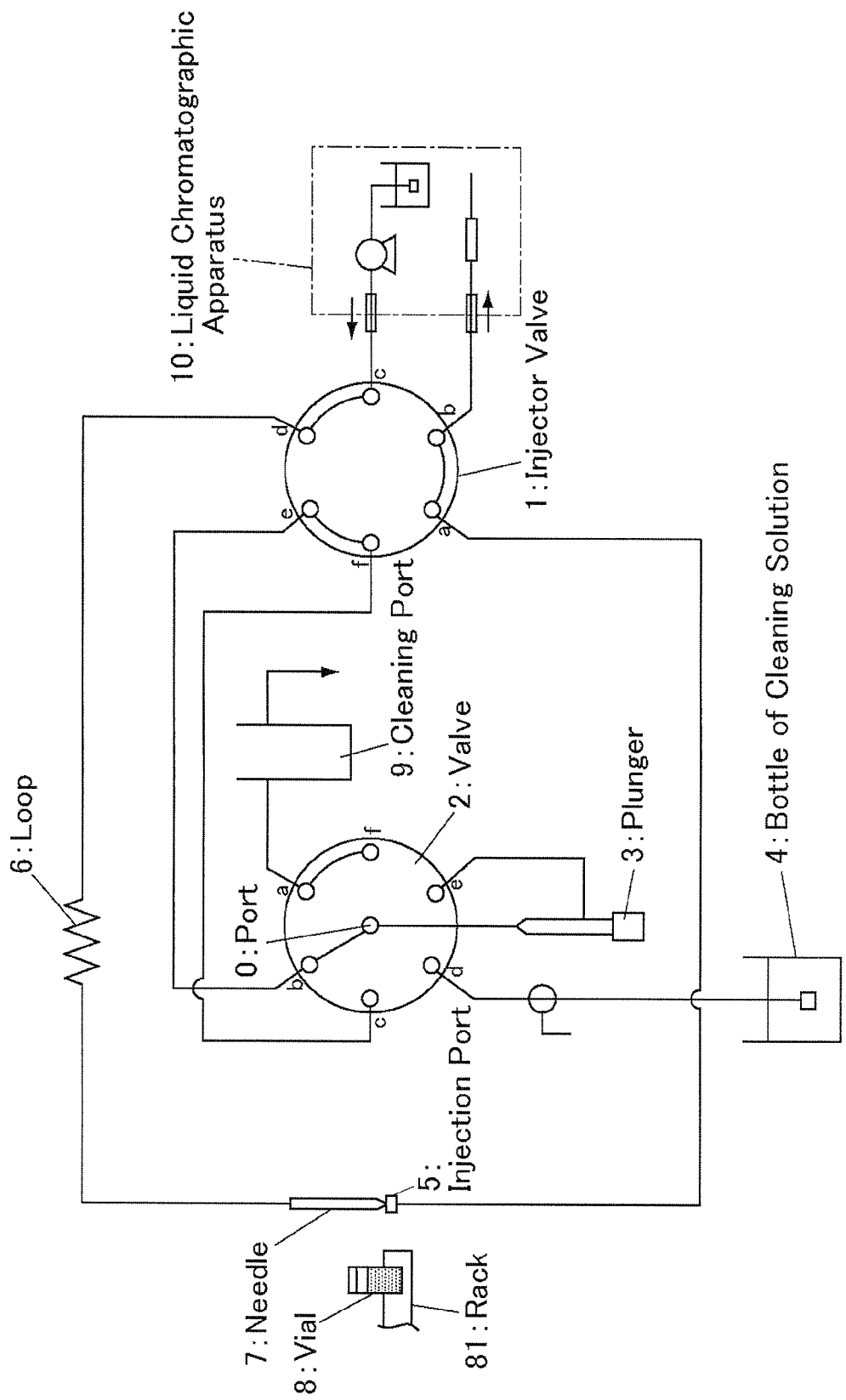
FIG. 5 is a schematic view showing the flow channels of an automatic sampler as an example to which the channel switching valve according to the present invention can be applied.

As shown in FIG. 5, the channel switching valve according to the present invention can be used in, for example, an automatic sampler for liquid chromatographic use. Liquid samples to be analyzed are previously sealed in vials (small-capacity sample bottles) 8 and placed on a rack 81. A needle 7 for collecting the samples from the vials 8 is connected through a flexible loop tube 6 (hereinafter, referred to as a "loop") to an injector valve 1. Further, the needle 7 is held by a driving mechanism (not shown), and therefore can be freely moved between each of the vials 8 and a cleaning port 9, between the cleaning port 9 and an injection port 5, and between the injection port 5 and each of the vials 8 in accordance with a program.

A valve 2 is a rotary 6-position valve to perform channel switching for suction and ejection of liquid by a plunger 3 connected to its common port. The plunger 3 is configured to reciprocally move by mechanical force. A cleaning solution bottle 4 is connected to one of the ports of the valve 2. The injector valve 1 is connected to a liquid chromatographic apparatus 10 through piping. The valve 1 is a 6-port valve to perform channel switching for introduction of a liquid sample into the flow of a liquid mobile phase.

The channel switching valve according to the present invention can be used as the valve 1 or valve 2 in such an automatic sampler as described above.

Hereinbelow, one example of a sequence of operations of sample injection using this automatic injector will be described.

(1) The injector valve 1 is brought into a state where the port "e" and the port "d" are interconnected. On the other hand, the valve 2 is brought into a state shown in FIG. 5 where the port "0" and the port "b" are interconnected. The needle 7 is inserted into the vial 8, and the plunger 3 is operated to suck a predetermined amount of liquid sample. The liquid sample sucked by the plunger 3 stays in the loop 6 and does not reach the valve 2 and the plunger 3.

(2) The needle 7 is removed from the vial 8 and is then moved to the injection port 5.

(3) The injector valve 1 is operated to be brought into a state shown in FIG. 5. The sample contained in the loop 6 is introduced into a flow channel of a liquid mobile phase to initiate liquid chromatographic analysis.

(4) The needle 7 is cleaned and is moved to the vial 8 containing the sample to be analyzed next, and then the operation steps (1) to (3) are repeated.

The application of the channel switching valve according to the present invention is not limited to such an automatic sampler as shown in FIG. 5 and can be widely used.

The channel switching valve according to the present invention can be used for high-performance liquid chromatographs as well as for analytical instruments and the like requiring channel switching.

What is claimed is:

1. A channel switching valve comprising:
a body section;
a stator to which a plurality of flow channels are to be connected and which has a surface having distribution ports to be connected to the flow channels respectively and is attached to the body section so that the surface faces inward;
a rotor which is placed in the body section, has a contact surface being in contact with the surface of the stator and having at least one groove for interconnecting two of the distribution ports of the stator, and is attached to a distal end of a shaft penetrating the body section so as to be rotated by rotation of the shaft to change a combination of the distribution ports that should be interconnected by the groove;
an elastic member held in the body section in its compressed state to urge the rotor toward the stator; and
an adjusting system which adjusts an urging force for pressing the rotor against the stator by changing a stroke of the elastic member,
wherein the adjusting system includes protruding/recessed patterns, the protruding/recessed patterns being designed to be fitted into each other,
wherein the stroke is changed between a first position in a state where the protruding/recessed patterns are fitted into each other and a second position in a state where the protruding/recessed patterns are not fitted into each other,
wherein the stator and the body section each have a connecting surface, and are removably fixed to each other by a fixing member at their connecting surfaces,
wherein one of the protruding/recessed patterns is formed on the connecting surface of the stator and the other of the protruding/recessed patterns is formed on the connecting surface of the body section, and
wherein by rotating the stator and the body section relative to each other, the stroke is changed between the first and second positions.

2. A channel switching valve comprising:
a body section;
a stator to which a plurality of flow channels are to be connected and which has a surface having distribution ports to be connected to the flow channels respectively and is attached to the body section so that the surface faces inward;
a rotor which is placed in the body section, has a contact surface being in contact with the surface of the stator and having at least one groove for interconnecting two of the distribution ports of the stator, and is attached to a distal end of a shaft penetrating the body section so as to be rotated by rotation of the shaft to change a combination of the distribution ports that should be interconnected by the groove;
an elastic member held in the body section in its compressed state to urge the rotor toward the stator; and
an adjusting system which adjusts an urging force for pressing the rotor against the stator by changing a stroke of the elastic member,
wherein the adjusting system includes protruding/recessed patterns, the protruding/recessed patterns being designed to be fitted into each other,
wherein the stroke is changed between a first position in a state where the protruding/recessed patterns are fitted into each other and a second position in a state where the protruding/recessed patterns are not fitted into each other,
wherein the rotor and the shaft each have a connecting surface, and are removably fixed to each other by a fixing member at their connecting surfaces,
wherein one of the protruding/recessed patterns is formed on the connecting surface of the rotor and the other of the protruding/recessed patterns is formed on the connecting surface of the shaft, and
wherein by rotating the rotor and the shaft relative to each other, the stroke is changed between the first and second positions.

* * * * *